United States Patent
Yates et al.

(10) Patent No.: US 7,329,877 B2
(45) Date of Patent: Feb. 12, 2008

(54) PHOTOELECTROCATALYTIC SENSOR FOR MEASURING OXIDIZABLE IMPURITIES IN AIR

(75) Inventors: Stephen F. Yates, Arlington Heights, IL (US); Brian C. Krafthefer, Stillwater, MN (US); Barrett E. Cole, Bloomington, MN (US)

(73) Assignee: Honeywell International, Inc., Morristown, NJ (US)

( * ) Notice: Subject to any disclaimer, the term of this patent is extended or adjusted under 35 U.S.C. 154(b) by 476 days.

(21) Appl. No.: 11/013,106

(22) Filed: Dec. 15, 2004

(65) Prior Publication Data

US 2006/0123885 A1    Jun. 15, 2006

(51) Int. Cl.
*G01J 1/42* (2006.01)
(52) U.S. Cl. ............................................. 250/373
(58) Field of Classification Search ............ 250/372, 250/373
See application file for complete search history.

(56) References Cited

U.S. PATENT DOCUMENTS

| | | | |
|---|---|---|---|
| 5,035,784 A | 7/1991 | Anderson et al. | |
| 5,045,288 A | 9/1991 | Raupp et al. | |
| 5,356,594 A | 10/1994 | Neel et al. | |
| 5,449,443 A | 9/1995 | Jacoby et al. | |
| 5,604,339 A | 2/1997 | Tabatabaie-Rassi et al. | |
| 5,677,190 A | 10/1997 | Melanson et al. | |
| 5,681,532 A | 10/1997 | Kane et al. | |
| 5,685,994 A * | 11/1997 | Johnson | 210/748 |
| 5,766,455 A | 6/1998 | Berman et al. | |
| 5,790,934 A | 8/1998 | Say et al. | |
| 5,835,840 A | 11/1998 | Goswami | |
| 5,842,110 A | 11/1998 | Tabatabaie-Raissi et al. | |
| 5,855,850 A * | 1/1999 | Sittler | 422/98 |
| 6,013,918 A * | 1/2000 | Bushnell et al. | 250/454.11 |
| 6,117,337 A | 9/2000 | Gonzalez-Martin et al. | |
| 6,433,957 B1 | 8/2002 | Rudd et al. | |
| 6,444,474 B1 * | 9/2002 | Thomas et al. | 436/146 |
| 6,491,883 B2 * | 12/2002 | Mori et al. | 422/306 |
| 6,582,666 B2 * | 6/2003 | Tabatabaie-Raissi et al. | 422/186 |
| 6,734,435 B2 * | 5/2004 | Sun et al. | 250/423 P |
| 6,752,957 B1 | 6/2004 | De Lasa et al. | |
| 7,166,259 B2 * | 1/2007 | Beam et al. | 422/186.04 |
| 2002/0037244 A1 * | 3/2002 | Takahashi et al. | 422/297 |
| 2002/0068017 A1 | 6/2002 | Naatz et al. | |
| 2002/0193064 A1 | 12/2002 | Michalakos et al. | |
| 2003/0066975 A1 * | 4/2003 | Okada | 250/492.2 |
| 2003/0087448 A1 | 5/2003 | Abe et al. | |
| 2003/0196692 A1 | 10/2003 | Koyanagi et al. | |

(Continued)

OTHER PUBLICATIONS

Wilson, Denise M., "Chemical Sensors for Portable, Handheld Field Instruments", IEEE Sensors Journal, vol. 1, No. 4, Dec. 2001, pp. 256-274.

(Continued)

Primary Examiner—David Porta
Assistant Examiner—David S Baker
(74) Attorney, Agent, or Firm—Oral Caglar, Esq.

(57) ABSTRACT

A photoelectrocatalytic sensor system for measuring oxidizable impurities in air. The sensor system may include a transistor having an electrode and a channel for the flow of current, a photocatalytic material coated onto the electrode of the transistor, a light source for producing an ultraviolet light beam onto the photocatalytic material, and a sensor for measuring the flow of current.

20 Claims, 2 Drawing Sheets

U.S. PATENT DOCUMENTS

2004/0022700 A1    2/2004   Kim et al.
2004/0067849 A1    4/2004   Tanaka et al.
2004/0197243 A1*  10/2004   Schwartz et al. ........ 422/186.3
2006/0034737 A1*   2/2006   Beam et al. ........... 422/186.07

OTHER PUBLICATIONS

Brown, Garrett N., "Development and Characterization of a Titanium Dioxide-Based Semiconductor Photoelectrochemical Detector", Analytical Chemistry, vol. 64, No. 4, Feb. 15, 1992, pp. 427-434.

Chasteen, Dr. Thomas G., "Photoionization Detector (PID)", Sam Houston State University, http://unx.1.shsu.edu/~chemistry/PID/PID.html, date unknown, 2 pg.

"Facts About PID Measurements", RAE Systems TN-102, date unknown, 3 pg.

Trautweiler, Stephan et al., "New Silicon-Based Metal-Oxide Chemical Sensors", Sensors, Sep. 1999, 8 pgs.

Whitaker, Tim, "SUVOS Pushes UV LEDS and Lasers To Shorter Wavelengths", Compound Semiconductor, date unknown.

* cited by examiner

PHOTOELECTROCATALYTIC SENSOR FOR MEASURING OXIDIZABLE IMPURITIES IN AIR

FIELD OF THE INVENTION

The invention relates generally to photoelectrocatalytic sensors, and more particularly to a photoelectrocatalytic sensor for measuring oxidizable impurities in air.

DESCRIPTION OF RELATED ART

Organic impurities, such as odors, volatile organic compounds (VOCs), toxic industrial chemicals (TICS), toxic industrial materials (TIMS), and chemical agents designed or known to be harmful to humans, can be impurities in air, especially in industrial or military environments. These organic compounds may need to be removed from the air to protect humans, or to enhance human comfort. Before these compounds can be removed from the air, these compounds must be detected. Some sensors have been developed to detect these compounds, however, very low concentrations of these organic impurities are difficult to detect in the air and sensors that detect these compounds are usually very bulky and some require ancillary equipment and conditioning.

Examples of sensors for organic impurities include mass spectrometers, flame ionization detectors, photoionization detectors and tin oxide sensors. Photoionization detectors use an ultraviolet (UV) light source with a wavelength of less than 200 nanometers (nm) for directly ionizing the organic molecules. A pair of electrodes is positioned adjacent to the UV light source and the change in the conductivity in the air is detected. Photoionization detectors are sensitive down to the parts per billion (ppb) range, but only for molecules which can be ionized directly using the UV light source. Tin oxide sensors contain crystals of tin oxide which are heated in air inside the sensor while an electric potential is applied. Absorbed oxygen at grain boundaries reduces the current flow through the crystal. When organic impurities are present in the air, these impurities react with this absorbed oxygen, increasing the current flow. Such sensors are much less sensitive than photoionization detectors.

Thus, it should be appreciated that a need exists for a sensor that can measure very low concentrations of organic impurities. The invention fulfills this need as well as others.

SUMMARY OF THE INVENTION

In particular, and by way of example only, one embodiment of the invention is a sensor for measuring oxidizable impurities that may include a light source configured to generate an ultraviolet light beam, an electronic device having a conductive surface, and a photocatalytic material coated onto the conductive surface of the electronic device for receiving the ultraviolet light beam.

One embodiment of the invention is a sensor system for measuring oxidizable impurities in air. The sensor system may include a transistor having an electrode and a channel for the flow of current, a photocatalytic material coated onto the electrode of the transistor, a light source for producing an ultraviolet light beam onto the photocatalytic material, and a sensor for measuring the flow of current.

One embodiment of the invention is a sensor-system for measuring oxidizable impurities in air. The sensor system may include a field effect transistor having an electrode, a first conductor and a second conductor, a titanium dioxide material contacting the electrode of the field effect transistor, and an ultraviolet light emitting diode to produce ultraviolet light directed toward the titanium dioxide material. The sensor system may also include a device to measure the amount of current traveling between the first conductor and the second conductor, and a channel to direct the flow of air through the ultraviolet light.

These and other features and advantages of the embodiments of the invention will become apparent from the following detailed description, taken in conjunction with the accompanying drawings, which illustrate, by way of example the principles of the invention.

DETAILED DESCRIPTION OF THE PREFERRED EMBODIMENTS

Systems and methods that implement the embodiments of the various features of the invention will now be described with reference to the drawings. The drawings and the associated descriptions are provided to illustrate embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "in one embodiment" in various places in the specification are not necessarily all referring to the same embodiment. Throughout the drawings, reference numbers are re-used to indicate correspondence between referenced elements. In addition, the first digit of each reference number indicates the figure in which the element first appears.

Figure 1:
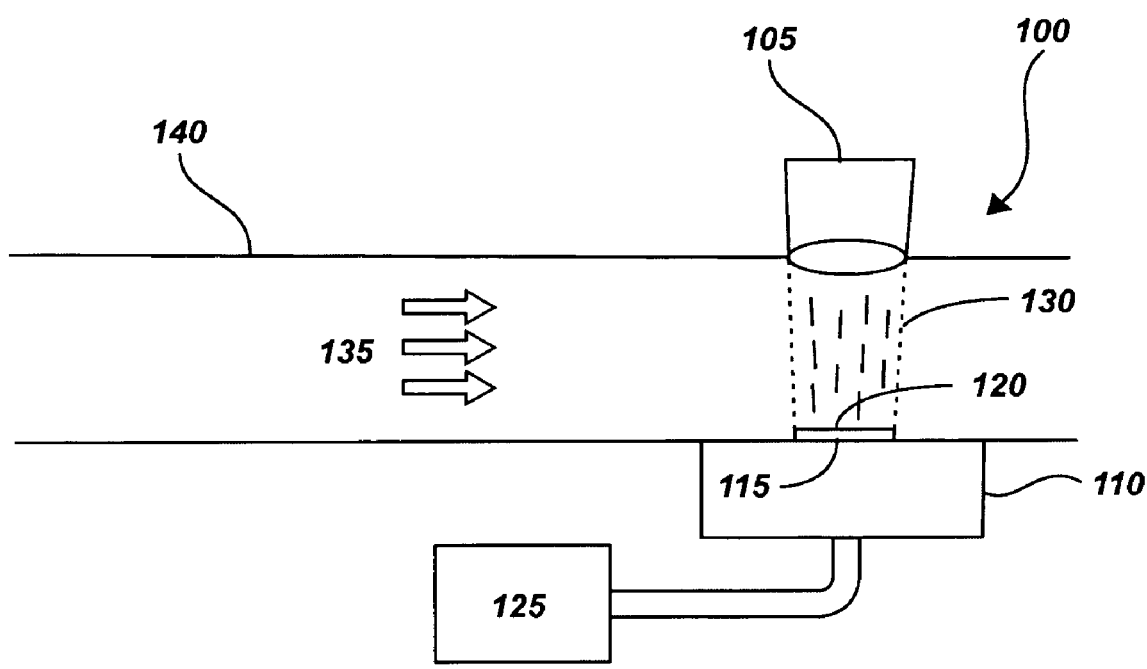
FIG. 1 is a simplified block diagram of a sensor system according to an embodiment of the invention.

Referring now more particularly to the drawings, FIG. 1 is a simplified block diagram of a sensor system 100 for measuring oxidizable impurities in air. In one embodiment, the sensor system 100 may be used to measure low concentrations, ranging from, for example, about 100 parts per million (ppm) to 1 ppb, of the oxidizable impurities. The oxidizable impurities may include odors, volatile organic compounds (VOCs), toxic industrial chemicals (TICS), toxic industrial materials (TIMS), and chemical agents designed or known to be harmful to human life.

The sensor system 100 may include a light source 105, an electronic device 110 having a conductive surface 115, a photocatalytic material 120, and a current detector 125. The light source 105 is capable of generating a light beam 130 that is directed toward the photocatalytic material 120. The light source 105 should be aimed or focused so that the light beam 130 substantially or completely covers the photocatalytic material 120. The light source 105 may be an ultraviolet (UV) lamp such as a mercury vapor lamp or a xenon lamp, an UV light emitting diode (LED), or an UV laser diode. For example, the light source 105 may be a LED capable of producing UV light having a wavelength of between about 200 nanometers (nm) and about 400 nm.

The light source 105 may be configured to generate a continuous or pulsed light beam 130. The light beam 130 may be pulsed to reduce the buildup of very high electrical charges on the conductive surface 115 and to reduce the power draw from the light source 105. When the light beam 130 is pulsed, the noise from external sources may be reduced because the current detector 125 can reject most of the electrical signals outside the desired frequency of the pulsed light beam 130.

In one embodiment, the intensity of the light source 105 is sufficient so that the photoreaction rate is not light-limited. The higher the intensity, the greater the signal from the photocatalytic material 120. The closer the light source 105 is to the photocatalytic material 120 or the more intense the light source 105, the more intense the light beam 130 is on the photocatalytic material 120. The linear distance between the light source 105 and the photocatalytic material 120 is preferably about one (1) centimeter, more preferably about fifty (50) millimeters (mm), and most preferably about ten (10) mm.

In various embodiments, the wavelength of the UV light is about 280 nm, 360 nm, 365 nm, 375 nm, 380 nm, and 390 nm. In various embodiments, the light source 105 can be UVLEDs such as model numbers NSHU550A (375 nm), NSHU550B (365 nm), NSHU590A (375 nm), and NSHU590B (365 nm), all manufactured by Nichia Corporation of Japan. In another embodiment, the light source 105 is a UVLED such as model LEDS built under the U.S. government SUVOS program, which has a wavelength of about 280 nm. The wavelength of the UVLED is set so that the UV light is absorbed by the photocatalytic material 120. That is, the wavelength of the UV light is matched to the absorption band of the photocatalytic material 120. For example, if the photocatalytic material 120 is a titanium dioxide having an absorption band of between about 200 nm and 400 nm, then the wavelength of the UVLED should be between about 250 nm and 390 nm. In another embodiment, if the photocatalytic material 120 is a titanium dioxide having an absorption band of less than about 410 nm, then the wavelength of the UVLED should be less than about 410 nm.

The electronic device 110 can be a semiconductor device (e.g., a field effect transistor (FET) or a metal oxide semiconductor field effect transistor (MOSFET)), an electrical component (e.g., a capacitor), or any other device capable of carrying or measuring an electrical current. The conductive surface 115 can be an electrode coated with an electrically conductive metallic material such as copper or platinum. The electrode controls the flow of current between a first junction (e.g., a source junction) and a second junction (e.g., a drain junction).

The photocatalytic material 120 is coated onto or connected to the conductive surface 115. The photocatalytic material 120 may be one or more of several different photocatalysts configured to absorb the UV light received from the light source 105. The photocatalytic material 120 uses the UV light to produce photocatalytic oxidation (i.e., to generate hydroxyl radicals from absorbed water). The photocatalytic material 120 may be a semiconductor photocatalyst such as titanium dioxide ($TiO_2$), zinc oxide (ZnO), cadmium sulfide (CdS), tantalum oxide ($Ta_2O_5$), or any other compound in which UV absorption results in the promotion of electrons to a conduction layer. For example, the photocatalytic material 120 can be Aeroxide $TiO_2$ P 25, manufactured by Degussa Corporation. In one embodiment, the photocatalytic material 120 has a surface area of between about 100-1000 square meters/gram and a thickness of between about 3.0 microns and about 5.0 microns. The photocatalytic material 120 should have a relatively large surface area and should be highly active.

The air 135 to be analyzed is directed through a passageway 140 and passed over the photocatalytic material 120. The air 135 should have good contact with the photocatalytic material 120. The good contact may be provided by adjusting the shape and size of the passageway 140. For example, in one embodiment, the passageway 140 may be formed in the shape of a cylinder and may have a diameter of between about 1-10 millimeters (mm). Additionally, the good contact may be provided by adjusting the velocity of the air 135 through the passageway 140 and/or making the interior surface of the passageway 140 rough. The photocatalytic material 120 may be formed to allow the air 135 to pass through or over it. For example, the photocatalytic material 120 may include a wire screen or a wire mesh through which the air 135 is forced to pass. In this embodiment, the photocatalytic material 120 is generally applied after the screen or mesh is coupled to the conductive surface 115.

The UV light is aimed or focused at the photocatalytic material 120 to irradiate the photocatalytic material 120. The oxidizable impurities in the air 135 are oxidized on the photocatalytic material 120 in a photoreaction powered by the UV light. When the photocatalytic material 120 is exposed to the UV light, electrons are promoted to the conduction band of the photocatalytic material 120, resulting in the holes and electrons moving independently of each other. In the absence of any other process, the holes and electrons normally recombine, resulting in no net change in the electrical charge. In the presence of absorbed water, the holes are converted to hydroxyl radicals, a short-lived and very powerful oxidant. If oxidizable impurities are also present, the oxidizable impurities are oxidized by the hydroxyl radicals, consuming the hydroxyl radicals. When such a chemical reaction occurs, the electrons that were promoted no longer have holes with which to recombine. In a conventional photocatalyst, the electrons are consumed by reaction with atmospheric oxygen in a relatively slow reaction. However, if the photocatalytic material 120 is coated onto the conductive surface 115, an electrical charge builds up on the photocatalytic material 120 and the conductive surface 115. The extent to which the conductive surface 115 becomes electrically charged is proportional to the extent of the chemical reaction between the oxidizable impurities and the photocatalytic material 120. The extent of the chemical reaction is proportional to the concentration of the oxidizable impurities. Hence, the greater the oxidizable impurities, the greater the electrical charge appearing on the photocatalytic material 120. The electrical charge on the conductive surface 115 may be measured by the current detector 125 or any other detection device or method.

The oxidizable impurities may include any chemical compound that has an oxidation potential lower than that of the hydroxyl radicals. The oxidizable impurities may absorb onto the photocatalytic material 120. Since the oxidation potential of the hydroxyl radicals is very high, the organic compounds and many inorganic compounds are oxidized and therefore detectable.

Figure 2:
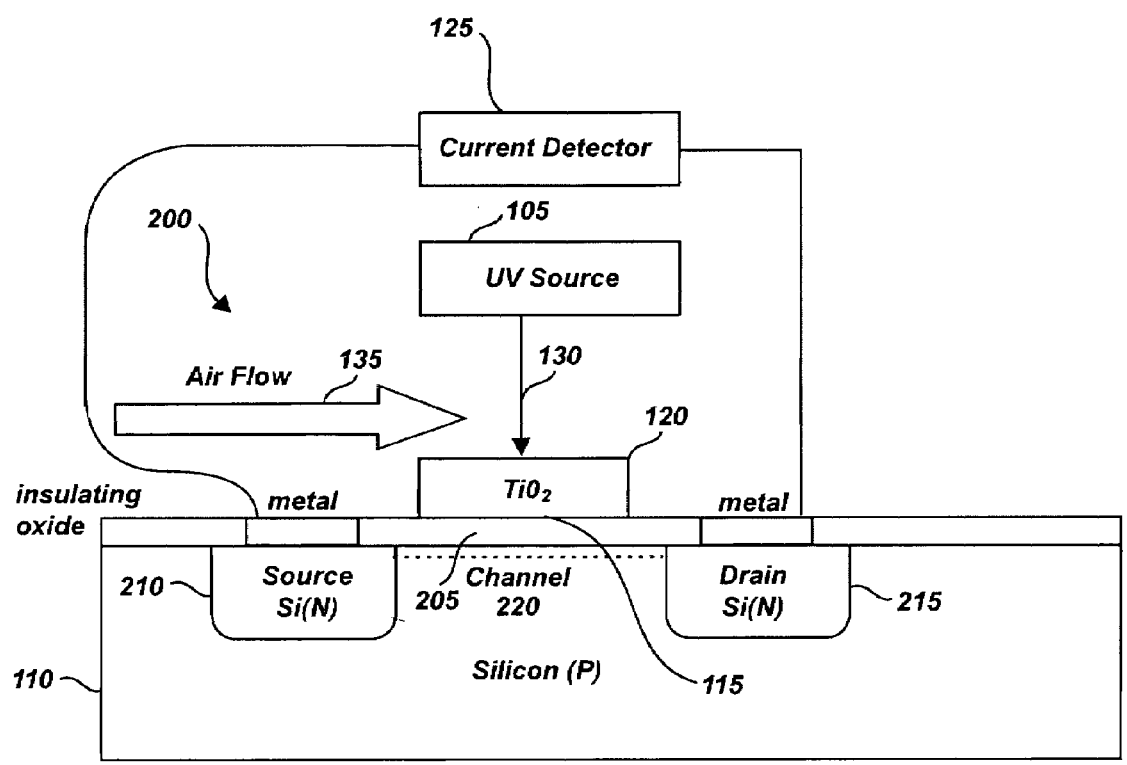
FIG. 2 is a cross-sectional view illustrating a sensor system where the electronic device is a MOSFET according to an embodiment of the invention.

FIG. 2 is a cross-sectional view illustrating a sensor system 200 where the electronic device 110 is a MOSFET. The photocatalytic material 120 is coated onto or connected to a gate junction 205 of the MOSFET. When the electrical charge is present on the conductive surface 115, the electrical charge turns on the gate junction 205 to allow the current to flow from a source junction 210 to a drain junction 215 forming a channel 220. The current detector 125 is connected to the source junction 210 and the drain junction 215 to measure the amount of current passing between the source junction 210 and the drain junction 215.

Although an exemplary embodiment of the invention has been shown and described, many other changes, combinations, omissions, modifications and substitutions, in addition to those set forth in the above paragraphs, may be made by one having skill in the art without necessarily departing from the spirit and scope of this invention. Accordingly, the invention is not intended to be limited by the preferred embodiments, but is to be defined by reference to the appended claims.

What is claimed is:

1. A sensor for measuring oxidizable impurities comprising:
    a light source configured to generate an ultraviolet light beam;
    an electronic device having a conductive surface;
    a photocatalytic material coated onto the conductive surface of the electronic device for receiving the ultraviolet light beam and generating a charge on the conductive surface; and
    a detector connected to the conductive surface and detecting said charge.

2. The sensor of claim 1 wherein said detector is a current detector.

3. The sensor of claim 1 wherein the ultraviolet light beam has a wavelength that is within an absorption band of the photocatalytic material.

4. The sensor of claim 1 wherein the light source is an ultraviolet lamp.

5. The sensor of claim 1 wherein the light source is an ultraviolet light emitting diode capable of generating the ultraviolet light beam having a wavelength of between 200 nanometers and 400 nanometers.

6. The sensor of claim 1 wherein the photocatalytic material is selected from a group consisting of titanium dioxide, zinc oxide, tantalum oxide, and cadmium sulfide.

7. The sensor of claim 1 further comprising a passageway to direct a flow of air through the ultraviolet light beam.

8. The sensor of claim 1 wherein the electronic device is [a transistor or] a capacitor.

9. The sensor of claim 1 wherein the conductive surface is an electrode.

10. The sensor of claim 1 wherein the ultraviolet light beam is a pulsed ultraviolet light beam.

11. The sensor of claim 1 wherein the photocatalytic material has a thickness of between 3 microns and 5 microns.

12. The sensor of claim 1 wherein the photocatalytic material is a semiconductor photocatalyst.

13. The sensor of claim 1 wherein the ultraviolet light beam is a continuous ultraviolet light beam.

14. A sensor system for measuring oxidizable impurities in air comprising:
    a transistor having an electrode and a channel for the flow of current;
    a photocatalytic material coated onto the electrode of the transistor;
    a light source for producing an ultraviolet light beam onto the photocatalytic material; and
    a sensor for measuring the flow of current.

15. The sensor system of claim 14 wherein the photocatalytic material is selected from a group consisting of titanium dioxide, zinc oxide, and cadmium sulfide.

16. The sensor system of claim 14 further comprising a passageway to direct the flow of air across the ultraviolet light beam.

17. The sensor system of claim 14 wherein the light source is an ultraviolet light emitting diode capable of producing the ultraviolet light beam having a wavelength of between 200 nanometers and 400 nanometers.

18. A sensor system for measuring oxidizable impurities in air comprising:
    a field effect transistor having an electrode, a first conductor and a second conductor;
    a titanium dioxide material contacting the electrode of the field effect transistor;
    an ultraviolet light emitting diode to produce ultraviolet light directed toward the titanium dioxide material;
    a device to measure the amount of current traveling between the first conductor and the second conductor; and
    a channel to direct the flow of air through the ultraviolet light.

19. The sensor system of claim 18 wherein the ultraviolet light has a wavelength of between 200 nanometers and 400 nanometers.

20. The sensor system of claim 18 wherein the electrode is a gate junction, the first conductor is a drain junction, and the second junction is a source junction.

* * * * *